United States Patent
Simpson et al.

(10) Patent No.: US 6,626,889 B1
(45) Date of Patent: Sep. 30, 2003

(54) THIN-WALLED GUIDING CATHETER WITH IMPROVED RADIOPACITY

(75) Inventors: John Arthur Simpson, Carlsbad, CA (US); Chris Lee Davis, San Marcos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/915,491

(22) Filed: Jul. 25, 2001

(51) Int. Cl.[7] ............................................... A61M 25/00
(52) U.S. Cl. ........................................ 604/524; 604/526
(58) Field of Search ................... 604/523–524, 604/158, 22, 47, 528, 95.01, 525, 264, 4, 104, 11, 103.05, 103, 69.01, 96, 101.05, 96.01, 101, 915; 606/108, 15, 585, 49, 192, 41, 104, 240, 198; 600/585, 114, 432

(56) References Cited

U.S. PATENT DOCUMENTS

| | | | |
|---|---|---|---|
| 4,990,138 A | * 2/1991 | Bacich et al. | 604/103.1 |
| 5,630,840 A | * 5/1997 | Mayer | 623/66.1 |
| 5,639,274 A | * 6/1997 | Fischell et al. | 604/104 |
| 5,769,830 A | * 6/1998 | Parker | 604/528 |
| 6,010,445 A | * 1/2000 | Armini et al. | 600/1 |
| 6,019,786 A | * 2/2000 | Thompson | 606/191 |
| 6,165,166 A | * 12/2000 | Samuelson et al. | 604/524 |

OTHER PUBLICATIONS

Dwyer et al, Delivery apparatus for a self–expanding stent, U.S. patent Publication No. US 2002/0016597 A1.*
Duerig et al, Stent, U.S. patent Publication No. US 2001/0007953 A1.*
Graf et al, Introducer Sheath, US patent Pub No. US 2001/0037065, Nov. 1, 2001.*
Advanced Materials & Processes, Dec. 1999, p. 29; 125–126.
*Molybdenum and Molybdenum Alloys*, Refractory Metals and Alloys, The Metalurgical Society of AIME, 1960, p. 343.

* cited by examiner

*Primary Examiner*—Brian L. Casler
*Assistant Examiner*—Roz Ghafoorian
(74) *Attorney, Agent, or Firm*—Fulwider Patton Lee & Utecht, LLP

(57) ABSTRACT

A thin walled intracorporeal catheter such as a guiding catheter employed for intravascular procedures which generally has an elongated catheter shaft with a polymeric wall with a stranded reinforcing structure having at least one strand and preferably most, if not all of the strands, formed of a metallic matereial containing at least 50%, preferably at least 65% by weight of a refractory metal such as molybdenum, tungsten rhenium, tantalum and niobium. The refractory metal containing strands of the reinforcing structure, which may have a circular or rectangular transverse cross-sectional shape, provide high levels of radiopacity with a high level of mechanical properties.

35 Claims, 1 Drawing Sheet

THIN-WALLED GUIDING CATHETER WITH IMPROVED RADIOPACITY

FIELD OF INVENTION

The invention relates to the field of intraluminal catheters, and particularly to guiding catheters suitable for intravascular procedures such as angioplasty, stent deployment, pacing lead deployment and the like.

BACKGROUND OF THE INVENTION

In percutaneous transluminal coronary angioplasty (PTCA) procedures a guiding catheter having a shaped distal section is percutaneously introduced into the patient's vasculature and then advanced through the patient's vasculature until the shaped distal section of the guiding catheter is adjacent to the ostium of a desired coronary artery. The proximal end of the guiding catheter, which extends out of the patient, is torqued to rotate the shaped distal section and, as the distal section rotates, it is guided into the desired coronary ostium. The distal section of the guiding catheter is shaped so as to engage a surface of the ascending aorta and thereby seat the distal end of the guiding catheter in the desired coronary ostium and to hold the catheter in that position during the procedures when other intravascular devices such as guidewires and balloon catheters are being advanced through the inner lumen of the guiding catheter.

In the typical PTCA or stent delivery procedures, the balloon catheter with a guidewire disposed within an inner lumen of the balloon catheter is advanced within the inner lumen of the guiding catheter which has been appropriately positioned with its distal tip seated within the desired coronary ostium. The guidewire is first advanced out of the distal end of the guiding catheter into the patient's coronary artery until the distal end of the guidewire crosses a lesion to be dilated or an arterial location where a stent is to be deployed. A balloon catheter is advanced into the patient's coronary anatomy over the previously introduced guidewire until the balloon on the distal portion of the balloon catheter is properly positioned across the lesion. Once properly positioned, the balloon is inflated with inflation fluid one or more times to a predetermined size so that in the case of the PTCA procedure, the stenosis is compressed against the arterial wall and the lumen dilated to open up the vascular passageway. In the case of stent deployment, the balloon is inflated to plastically expand the stent within the stenotic region where it remains in the expanded condition. Generally, the inflated diameter of the balloon is approximately the same diameter as the native diameter of the body lumen being dilated so as to complete the dilatation or stent deployment but not overexpand the artery wall. After the balloon is finally deflated, blood flow resumes through the dilated artery and the dilatation catheter and the guidewire can be removed therefrom.

Generally, the stent deployment may be accomplished simultaneously with or after a PTCA procedure has been performed at the stenotic site.

In addition to their use in PTCA and stent delivery procedures, guiding catheters are used to advance a variety of electrophysiology-type catheters and other therapeutic and diagnostic devices into the coronary arteries, the coronary sinus, the heart chambers, neurological and other intracorporeal locations for sensing, pacing, ablation and other procedures. For example, one particularly attractive procedure for treating patients with congestive heart failure (CHF) involves introduction of a pacing lead into the patient's coronary sinus and advancing the lead through the patient's great coronary vein and a branch of the great coronary vein until the distal end of the pacing lead is disposed at a location which allows the electrical impulse from the pacing lead to pace the left ventricle of the patient's heart. A second pacing lead may be disposed within the patient's right ventricle or a cardiac vein draining the patient's right ventricle and both the left and right ventricle may then be paced by the pacing leads, resulting in greater pumping efficiencies and greater blood flow out of the heart which minimizes the effects of CHF.

Current construction of many commercially available guiding catheters include an elongated shaft of a polymeric tubular member with reinforcing strands (usually made of metal, high strength polymers or combinations thereof) within the wall of the tubular member. The strands are usually braided or wound into a reinforcing structure.

Clinical requirements for utilizing guiding catheters to advance catheters and other intravascular devices have resulted in a need for increased transverse dimensions of the inner lumens of guiding catheters to accommodate a greater variety of larger intracorporeal devices and for decreased outer transverse dimensions of the guiding catheter to present a lower profile which facilitates further advancement within the patient's body lumens and openings. These catheter design changes have required a reduction in the wall thickness which in turn requires a reduction in the ratio of polymer to stranded reinforcement and a reduction in the strand thickness. This all results in a catheter shaft which is not very visible fluoroscopically due to the low level of radiopacity.

What has been needed is a catheter design which would allow for continued thinning of the catheter wall for increased lumen size and lower outer profiles, while providing the strength and radiopacity levels that are clinically desirable for such products. The present invention satisfies these and other needs.

SUMMARY OF THE INVENTION

The invention is generally directed to a thin walled intraluminal catheter such as a guiding catheter with a multistrand reinforcing structure which has improved radiopacity with little or no reduction in structural properties of the catheter wall.

The guiding catheter of the invention has an elongated shaft with a preshaped distal shaft section to facilitate placement of the distal tip of the catheter. The shaft has a multistrand reinforcement, preferably within the wall of the shaft, which may be braided or wound. At least one of the strands of the reinforcing structure is formed of an alloy having at least 50% by weight, preferably at least 65% by weight of one or more suitable refractory metals. Suitable refractory metals include molybdenum, tungsten, rhenium, tantalum and niobium.

The radiopacity of a refractory metal generally follows the mass density of the metal, the greater the mass density the greater the radiopacity. However, the mechanical properties, i.e. elastic modulus, of the refractory metals do not follow the mass density. The mass density, elastic modulus and relative costs of suitable refractory metals and stainless steel (for comparison) are provided in the table below.

| REFRACTORY METAL | MASS DENSITY (lb/cu. in.) | ELASTIC MODULUS (Mpsi) | RELATIVE COSTS |
|---|---|---|---|
| Rhenium | 0.760 | 67 | High |
| Tungsten | 0.695 | 58 | Moderately High |
| Tantalum | 0.600 | 26.8 | High |
| Molybdenum | 0.369 | 47 | Medium |
| Niobium | 0.310 | 14.9 | High |
| 304 Stainless Steel | 0.286 | 28 | Low |

From the table above it becomes clear that rhenium and tungsten are very suitable metals, but their relatively high cost may preclude some applications. Tantalum has very good radiopacity but has relatively low strength and high costs. Niobium has marginally good radiopacity when compared to stainless steel but it is expensive and has lower mechanical properties than stainless steel. As a result niobium would have limited usage. Molybdenum has moderately high radiopacity, good mechanical properties and moderate cost and because of this combination of features will have more widespread usage than most of the other refractory metals.

Molybdenum containing strand material may be the metal alone or alloys thereof. Suitable alloying metals include tungsten, zirconium and halfnium. Preferably, tungsten may be included in amounts up to 30% (by wt), zirconium in amounts up to about 0.6% (by wt) and halfnium in amounts up to about 1% (by wt). Other alloying metal may also be utilized with molybedenum.

The radiopacity of the catheter is a function of both the level of radiopaque elements in the alloy, i.e. the refractory metal content, of the strands and the number and thickness of strands containing refractory metals. For adequate radiopacity at least 25% of the strands, preferably 75% of the strands of the reinforcing structure should be formed of the refractory metal containing material.

The elongated catheter shaft may have varied properties along the length. Typically, the elongated catheter shaft has increased flexibility in the distal direction by forming the catheter wall with polymeric materials having decreasing stiffness, i.e. distally decreasing durometers.

One embodiment of the catheter shaft having features of the invention includes a polymeric tube which forms the inner lining for the catheter shaft having multiple strands (e.g. 4 to 32 strands, typically 12, 16 or 24 strands) of suitable material in the form of wire or ribbon. Preferably, the strands are braided or wound about the inner tubular member. A sufficient number of the strands are formed of refractory metal containing material to provide a reinforcing structure having a desired radiopacity and providing the desire mechanical properties to the catheter. An outer polymer jacket may then be provided on the exterior of the reinforcing structure by suitable means such as heat shrinking, extruding or dip forming a polymeric layer onto the surface of the reinforcing structure. A removable mandrel may be provided within the inner lumen defined by the inner lining during the manufacturing process to shape the catheter into its desired configuration while it is being formed. The strands which make up the reinforcing structure may be suitable secured together to form the multistrand reinforcement into a stiffer structure. A plurality of the cross points, where the individual strands cross, may be secured together by brazing, soldering, welding, suitable mechanical connections and the like to form the stiffer structure.

The braided or wound multistrand reinforcing structure extends through most of the length of the elongated catheter shaft except for the distal tip which is usually provided with relatively flexible non-reinforced polymeric tubular member to provide non-traumatic characteristics to the distal tip.

Providing a plurality of strands formed of the refractory metal containing material within the reinforcement structure strengthens the structure and minimizes the support the polymeric material must add to the catheter shaft structure. This allows for much thinner polymer layers, resulting in thinner catheter walls and provides for more supportive and consistent catheter shapes. In addition the strands formed of refractory metal containing materials within the multistrand reinforcing structure of the catheter provide increased radiopacity over other strands previously used.

These and other advantages of the invention will become more apparent from the following detailed description of the invention and the accompanying exemplary drawings.

DETAILED DESCRIPTION OF THE INVENTION

Figure 1:
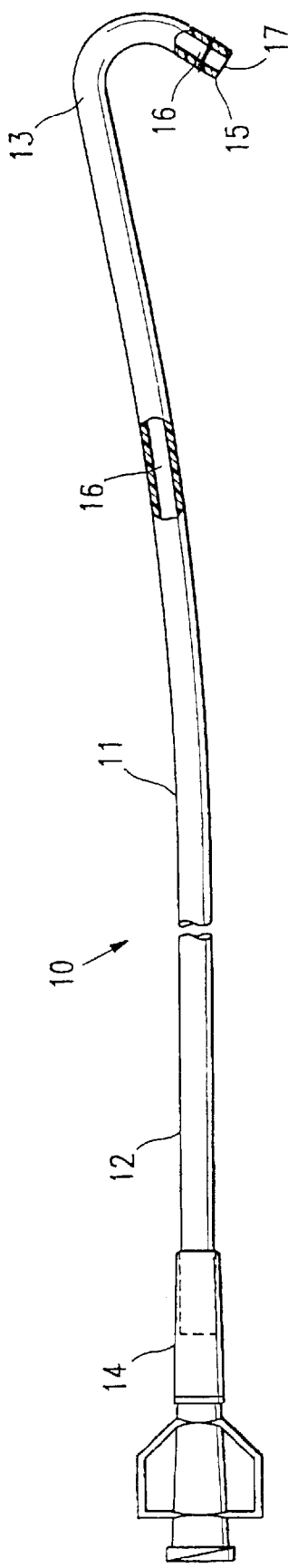
FIG. 1 is a schematic, elevational view of a guiding catheter embodying features of the invention.

FIG. 1 illustrates a catheter 10 embodying features of the invention which generally includes an elongated catheter shaft 11 with a proximal shaft section 12 and a shaped distal shaft section 13, an adapter 14 mounted on the proximal end of proximal shaft section 12, a non-traumatic distal tip 15 and an inner lumen 16 which extends within the catheter shaft 11 from the proximal end thereof to a port 17 located in the distal end of the shaft.

Figure 2:
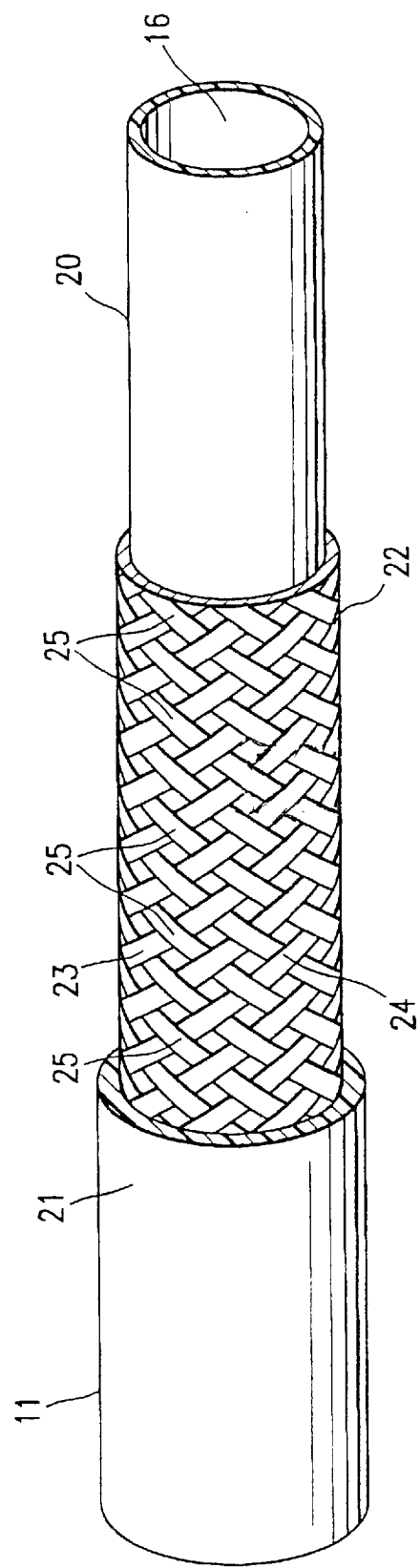
FIG. 2 is a partial cutaway perspective view of the elongated shaft of the catheter shown in FIG. 1.

As shown in greater detail in FIG. 2, the elongated catheter shaft 11 is formed of inner polymeric layer 20, an outer polymeric layer 21 and a braided reinforcing structure 22 formed of multiple strands 23 disposed between the inner and outer polymeric layers. The reinforcing structure 22 may be stiffened by securing strands 23 together at their crosspoints 25. The strands may be secured together by welding, brazing, soldering, adhesives or mechanically.

Guiding catheters designed for coronary artery access generally have a length from about 90 to about 130 cm, preferably about 100 to about 120 cm. The wall thickness of the catheter shaft ranges from about 0.003 to about 0.01 inch (0.076–0.254 mm). The thickness of the outer polymeric layer is about 0.0005 to about 0.006 inch (0.013–0.152 mm), preferably about 0.001 to about 0.003 inch (0.025–0.076 mm). The inner polymeric layer thickness is about 0.0005 to about 0.002 inch (0.013–0.051 mm), preferably about 0.0007 to about 0.0012 inch (0.018–0.031 mm).

The strands which are braided or wound to form the reinforcing structure may have a round (wire) or rectangular (ribbon) and their dimensions depends upon their mechanical properties and the stiffness and radiopacity desired. Wire diameters of about 0.0005 to about 0.003 inch (0.013–0.076 mm) are suitable. For ribbons, the transverse cross sectional dimensions are about 0.0005 to about 0.002 (0.013–0.076 mm) by about 0.003 to about 0.01 inch (0.076–0.25 mm). The maximum wall thickness of the braided reinforcing structure will be located at the cross points of the strands. The transverse and longitudinal dimensions of the catheter, the materials of construction, the number, size, spacing and molybdenum content of the reinforcing strands will vary depending upon the end use of the catheter.

While most of the strands forming the braided reinforcing structure should preferably formed of molybdenum or molybdenum alloys, up to 50% of the strands can be formed of a variety of other materials include stainless steel (304) and high strength alloys such as MP35N, Elgiloy and L-605 which contain cobalt, chromium and nickel. The high strength alloys generally contain about 28 to about 65% cobalt, about 2 to about 40% nickel, about 5 to about 35% chromium and preferably also contain up to about 12% molybdenum, up to about 20% tungsten, up to about 20% iron and inconsequential amounts of other elements either as positive additions or impurities. The high strength alloy strands are preferably precipitation hardened for optimum properties. High strength plastic strands (e.g. Kevlar) or mixtures of plastic and metallic strands may also be used to form part of the multistrand reinforcing structure.

The adapter 16 on the proximal end of the catheter and the nose piece for the adapter may be formed of conventional polymeric materials such as polycarbonate.

The inner layer 20 of the shaft 11 is preferably formed of lubricous material or have a lubricious inner surface. The presently preferred lubricious material is a fluoropolymer. Depending upon wall thickness requirements, the outer layer 21 may be a polyimide such as film-dipped thermosets for extremely thin walls or a polyamide elastomer, e.g. a polyether block amide such as PEBAX 55 alone or blended with nylon or PEBAX materials with other durometers for conventional wall thicknesses. The presently suitable polymeric materials are various durometers of PEBAX or nylon. Other suitable polymeric materials for the outer layer 21 include polyurethanes. A variety of other thermoplastic and thermoelastic polymers, copolymers and blends may also be employed.

It will be apparent from the foregoing that, while particular forms of the invention have been illustrated and described, various modifications can be made without departing from the spirit and scope of the invention. Moreover, those skilled in the art will recognize that features shown in one embodiment of the invention may be utilized in other embodiments of the invention. To the extent not otherwise described herein, the materials and methods of construction and the dimensions of conventional intravascular guidewires may be employed with the guiding member embodying features of the present invention. While the description of the invention is directed to embodiments for coronary applications, various modifications and improvements can be made to the invention without departing therefrom. Additionally, reference to the terms "members", "elements", "sections" and terms of similar import in the claims which follow shall not be interpreted to invoke the provisions of 35 U.S.C. §112(paragraph 6) unless reference is expressly made to the term "means" followed by an intended function.

What is claimed is:

1. An intraluminal catheter comprising an elongated shaft having proximal and distal ends, a port in the distal end, a wall defining an inner lumen extending within the elongated shaft which is in fluid communication with the port in the distal end and a multistrand reinforcement within the wall having at least one strand formed of a metallic material containing at least 50% (by weight) of a refractory metal selected from a group consisting of molybdenum, tungsten, rhenium, tantalum and niobium.

2. The intraluminal catheter of claim 1 wherein the refractory metal has a mass density greater than 0.3 pounds/inch$^3$.

3. The intraluminal catheter of claim 1 wherein the refractory metal has an elastic modulus greater than $30\times10^6$ psi.

4. The intraluminal catheter of claim 1 wherein the refractory metal is niobium.

5. The intraluminal catheter of claim 1 wherein the refractory metal is molybdenum.

6. The intraluminal catheter of claim 1 wherein the refractory metal is tungsten.

7. The intraluminal catheter of claim 1 wherein the refractory metal is tantalum.

8. The intraluminal catheter of claim 1 wherein the refractory metal is rhenium.

9. The intraluminal catheter of claim 1 wherein at least one strand is formed of an alloy containing at least 75% (by weight) of a refractory metal.

10. The intraluminal catheter of claim 9 wherein the refractory metal is molybdenum.

11. The intraluminal catheter of claim 1 wherein the multistrand reinforcement has between about 4 and 32 strands.

12. The intraluminal catheter of claim 1 wherein the multistrand reinforcement has between about 12 and 24 strands.

13. The intraluminal catheter of claim 1 wherein at least half of the strands in the multistrand reinforcement are formed of a metallic material containing at least 50% (by weight) molybdenum.

14. The intraluminal catheter of claim 1 wherein at least half of the strands in the multistrand reinforcement are formed of a metallic material containing at least 65% (by weight) molybdenum.

15. The intraluminal catheter of claim 12 wherein at least half of the strands in the multistrand reinforcement are formed of a metallic material containing tungsten and at least 65% (by weight) molybdenum.

16. The intraluminal catheter of claim 1 wherein the wall is formed of an inner layer and an outer layer with the multistrand reinforcement disposed between the inner and outer layer.

17. The intraluminal catheter of claim 16 wherein the inner layer is formed of lubricious material.

18. The intraluminal catheter of claim 16 wherein the outer layer is formed of a polymeric material selected from a group comprising polyimide and polyester.

19. The intraluminal catheter of claim 1 wherein the at least one strand has a circular transverse cross-section.

20. The intraluminal catheter of claim 8 wherein the at least one strand has a diameter between about 0.0005 to about 0.002 inch.

21. The intraluminal catheter of claim 1 wherein the at least one strand has a rectangular transverse cross-section.

22. The intraluminal catheter of claim 10 wherein the at least one strand has a short transverse dimension of about 0.0005 to about 0.002 inch.

23. The intraluminal catheter of claim 10 wherein the at least one strand has a long transverse dimension of about 0.002 to about 0.01 inch.

24. The intraluminal catheter of claim 1 wherein a plurality of strands of the multistranded reinforcement are braided.

25. The intraluminal catheter of claim 1 wherein the strands of the multistranded reinforcement are wound.

26. The intraluminal catheter of claim 1 having a nontraumatic distal tip.

27. The intraluminal catheter of claim 1 having a length between about 90 and 130 cm.

28. The intraluminal catheter of claim 1 having a shaped distal extremity.

29. A guiding catheter for accessing coronary blood vessels, comprising:
   a. an elongated shaft having proximal and distal ends, a port in the distal end, a wall defining an inner lumen extending within the elongated shaft which is in fluid communication with the port in the distal end and a multistrand reinforcement within the wall having at least one strand formed of a metallic material containing at least 50% (by weight) of a refractory metal selected from a group consisting of molybdenum, tungsten, rhenium, tantalum and niobium;
   b. an adapter on the proximal end in fluid communication the inner lumen extending within the elongated shaft; and
   c. a non-traumatic distal tip defining the port in the distal end.

30. The guiding catheter of claim 29 wherein the refractory alloy is tantalum.

31. The guiding catheter of claim 29 wherein the refractory metal is molybdenum.

32. The guiding catheter of claim 29 wherein the refractory metal is tungsten.

33. The guiding catheter of claim 29 wherein the refractory metal is rhenium.

34. The guiding catheter of claim 29 wherein at least one strand is formed of an alloy containing at least 75% (by weight) of a refractory metal.

35. An intraluminal catheter comprising an elongated shaft having proximal and distal ends, a port in the distal end, a wall defining an inner lumen extending within the elongated shaft which is in fluid communication with the port in the distal end and a multistrand reinforcement within the wall having at least one strand formed of an alloy containing at least 75% by weight of a refractory metal.

* * * * *